US012558093B2

(12) United States Patent
Beardsley et al.

(10) Patent No.: US 12,558,093 B2
(45) Date of Patent: Feb. 24, 2026

(54) SURGICAL STAPLING DEVICE WITH FLOATING STAPLE CARTRIDGE

(71) Applicant: Covidien LP, Mansfield, MA (US)

(72) Inventors: John Beardsley, Wallingford, CT (US); Stanislaw Kostrzewski, Newton, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/213,391

(22) Filed: Jun. 23, 2023

(65) Prior Publication Data

US 2023/0329712 A1 Oct. 19, 2023

Related U.S. Application Data

(63) Continuation of application No. 17/712,748, filed on Apr. 4, 2022, now abandoned, which is a continuation
(Continued)

(51) Int. Cl.
*A61B 17/072* (2006.01)
*A61B 17/00* (2006.01)

(52) U.S. Cl.
CPC .................. *A61B 17/07207* (2013.01); *A61B 2017/00862* (2013.01); *A61B 2017/00951* (2013.01);
(Continued)

(58) Field of Classification Search
CPC ........ A61B 17/07292; A61B 17/07207; A61B 2017/00862; A61B 2017/07242
See application file for complete search history.

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

AU 198654765 9/1986
CA 2773414 A1 11/2012
(Continued)

OTHER PUBLICATIONS

European Search Report dated Jan. 25, 2019, issued in EP Appln. No. 18190298.
(Continued)

*Primary Examiner* — Veronica Martin

(57) ABSTRACT

A surgical stapling device includes tool assembly having an anvil assembly and a cartridge assembly including a cartridge channel and a staple cartridge supported within the cartridge channel. The cartridge channel has a pair of spaced sidewalls and a bottom wall. The cartridge assembly includes compression strips that are supported on upper edges of the side walls and are positioned to support the staple cartridge. In embodiments, each of the compression strips includes a connecting portion and the upper edge of each of the side walls defines a slot that is configured to receive the connecting portion of a respective compression strip to secure the compression strip to the side wall of the cartridge channel. In some embodiments, the tool assembly also includes a compressible pad that is supported on the bottom wall of the cartridge channel between the bottom of the cartridge channel and the staple cartridge.

18 Claims, 10 Drawing Sheets

Related U.S. Application Data of application No. 16/829,379, filed on Mar. 25, 2020, now abandoned, which is a continuation of application No. 15/684,223, filed on Aug. 23, 2017, now Pat. No. 10,624,636.

(52) U.S. Cl.
CPC ............... *A61B 2017/07242* (2013.01); *A61B 2017/0725* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01)

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |

(56) References Cited

U.S. PATENT DOCUMENTS

| | | | |
|---|---|---|---|
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |

(56)                 References Cited

U.S. PATENT DOCUMENTS

| | | | |
|---|---|---|---|
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |

(56)     References Cited

U.S. PATENT DOCUMENTS

| | | | |
|---|---|---|---|
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |

(56) References Cited

U.S. PATENT DOCUMENTS

| | | | |
|---|---|---|---|
| 7,913,891 | B2 | 3/2011 | Doll et al. |
| 7,913,893 | B2 | 3/2011 | Mastri et al. |
| 7,914,543 | B2 | 3/2011 | Roth et al. |
| 7,918,230 | B2 | 4/2011 | Whitman et al. |
| 7,922,061 | B2 | 4/2011 | Shelton, IV et al. |
| 7,922,063 | B2 | 4/2011 | Zemlok et al. |
| 7,922,064 | B2 | 4/2011 | Boyden et al. |
| 7,926,691 | B2 | 4/2011 | Viola et al. |
| 7,926,692 | B2 | 4/2011 | Racenet et al. |
| 7,934,628 | B2 | 5/2011 | Wenchell et al. |
| 7,934,630 | B2 | 5/2011 | Shelton, IV et al. |
| 7,934,631 | B2 | 5/2011 | Balbierz et al. |
| 7,942,300 | B2 | 5/2011 | Rethy et al. |
| 7,942,303 | B2 | 5/2011 | Shah |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,954,682 | B2 | 6/2011 | Giordano et al. |
| 7,954,683 | B1 | 6/2011 | Knodel et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,959,051 | B2 | 6/2011 | Smith et al. |
| 7,963,431 | B2 | 6/2011 | Scirica |
| 7,963,432 | B2 | 6/2011 | Knodel et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,975,894 | B2 | 7/2011 | Boyden et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,215,532 | B2 | 7/2012 | Marczyk |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |

(56) References Cited

U.S. PATENT DOCUMENTS

| | | | |
|---|---|---|---|
| 8,276,594 | B2 | 10/2012 | Shah |
| 8,276,801 | B2 | 10/2012 | Zemlok et al. |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |
| 8,292,153 | B2 | 10/2012 | Jankowski |
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |
| 8,317,070 | B2 | 11/2012 | Hueil et al. |
| 8,317,071 | B1 | 11/2012 | Knodel |
| 8,322,455 | B2 | 12/2012 | Shelton, IV et al. |
| 8,322,589 | B2 | 12/2012 | Boudreaux |
| 8,328,061 | B2 | 12/2012 | Kasvikis |
| 8,328,065 | B2 | 12/2012 | Shah |
| 8,333,313 | B2 | 12/2012 | Boudreaux et al. |
| 8,336,751 | B2 | 12/2012 | Scirica |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,353,437 | B2 | 1/2013 | Boudreaux |
| 8,353,440 | B2 | 1/2013 | Whitman et al. |
| 8,356,740 | B1 | 1/2013 | Knodel |
| 8,357,174 | B2 | 1/2013 | Roth et al. |
| 8,360,294 | B2 | 1/2013 | Scirica |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,365,971 | B1 | 2/2013 | Knodel |
| 8,365,972 | B2 | 2/2013 | Aranyi et al. |
| 8,365,973 | B1 | 2/2013 | White et al. |
| 8,365,976 | B2 | 2/2013 | Hess et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,381,828 | B2 | 2/2013 | Whitman et al. |
| 8,381,961 | B2 | 2/2013 | Holsten et al. |
| 8,387,848 | B2 | 3/2013 | Johnson et al. |
| 8,387,849 | B2 | 3/2013 | Buesseler et al. |
| 8,387,850 | B2 | 3/2013 | Hathaway et al. |
| 8,388,652 | B2 | 3/2013 | Viola |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,397,971 | B2 | 3/2013 | Yates et al. |
| 8,397,972 | B2 | 3/2013 | Kostrzewski |
| 8,403,195 | B2 | 3/2013 | Beardsley et al. |
| 8,403,196 | B2 | 3/2013 | Beardsley et al. |
| 8,403,197 | B2 | 3/2013 | Vidal et al. |
| 8,403,198 | B2 | 3/2013 | Sorrentino et al. |
| 8,403,956 | B1 | 3/2013 | Thompson et al. |
| 8,408,439 | B2 | 4/2013 | Huang et al. |
| 8,408,440 | B2 | 4/2013 | Olson et al. |
| 8,408,442 | B2 | 4/2013 | Racenet et al. |
| 8,413,868 | B2 | 4/2013 | Cappola |
| 8,413,869 | B2 | 4/2013 | Heinrich |
| 8,413,871 | B2 | 4/2013 | Racenet et al. |
| 8,418,904 | B2 | 4/2013 | Wenchell et al. |
| 8,418,905 | B2 | 4/2013 | Milliman |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,419,768 | B2 | 4/2013 | Marczyk |
| 8,424,735 | B2 | 4/2013 | Viola et al. |
| 8,424,736 | B2 | 4/2013 | Scirica et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,439,244 | B2 | 5/2013 | Holcomb et al. |
| 8,439,245 | B2 | 5/2013 | Knodel et al. |
| 8,439,246 | B1 | 5/2013 | Knodel |
| 8,444,036 | B2 | 5/2013 | Shelton, IV |
| 8,444,037 | B2 | 5/2013 | Nicholas et al. |
| 8,444,038 | B2 | 5/2013 | Farascioni et al. |
| 8,448,832 | B2 | 5/2013 | Viola et al. |
| 8,453,652 | B2 | 6/2013 | Stopek |
| 8,453,905 | B2 | 6/2013 | Holcomb et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,909 | B2 | 6/2013 | Olson et al. |
| 8,453,910 | B2 | 6/2013 | Bettuchi et al. |
| 8,453,912 | B2 | 6/2013 | Mastri et al. |
| 8,453,913 | B2 | 6/2013 | Milliman |
| 8,453,914 | B2 | 6/2013 | Laurent et al. |
| 8,454,628 | B2 | 6/2013 | Smith et al. |
| 8,459,520 | B2 | 6/2013 | Giordano et al. |
| 8,459,521 | B2 | 6/2013 | Zemlok et al. |
| 8,459,522 | B2 | 6/2013 | Marczyk |
| 8,459,523 | B2 | 6/2013 | Whitman |
| 8,459,524 | B2 | 6/2013 | Pribanic et al. |
| 8,459,525 | B2 | 6/2013 | Yates et al. |
| 8,464,922 | B2 | 6/2013 | Marczyk |
| 8,464,923 | B2 | 6/2013 | Shelton, IV |
| 8,469,252 | B2 | 6/2013 | Holcomb et al. |
| 8,469,254 | B2 | 6/2013 | Czernik et al. |
| 8,474,677 | B2 | 7/2013 | Woodard, Jr. et al. |
| 8,479,967 | B2 | 7/2013 | Marczyk |
| 8,479,968 | B2 | 7/2013 | Hodgkinson et al. |
| 8,479,969 | B2 | 7/2013 | Shelton, IV |
| 8,485,412 | B2 | 7/2013 | Shelton, IV et al. |
| 8,490,852 | B2 | 7/2013 | Viola |
| 8,496,152 | B2 | 7/2013 | Viola |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,499,993 | B2 | 8/2013 | Shelton, IV et al. |
| 8,505,799 | B2 | 8/2013 | Viola et al. |
| 8,505,802 | B2 | 8/2013 | Viola et al. |
| 8,511,575 | B2 | 8/2013 | Cok |
| 8,512,359 | B2 | 8/2013 | Whitman et al. |
| 8,512,402 | B2 | 8/2013 | Marczyk et al. |
| 8,517,240 | B1 | 8/2013 | Mata et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,523,041 | B2 | 9/2013 | Ishitsuki et al. |
| 8,523,042 | B2 | 9/2013 | Masiakos et al. |
| 8,523,043 | B2 | 9/2013 | Ullrich et al. |
| 8,534,528 | B2 | 9/2013 | Shelton, IV |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,733 | B2 | 9/2013 | Whitman et al. |
| 8,544,711 | B2 | 10/2013 | Ma et al. |
| 8,550,325 | B2 | 10/2013 | Cohen et al. |

(56)                  References Cited

U.S. PATENT DOCUMENTS

| | | | |
|---|---|---|---|
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 * | 2/2015 | Zemlok .......... A61B 17/07207 |
| | | 227/176.1 |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |

(56) References Cited

U.S. PATENT DOCUMENTS

| | | | |
|---|---|---|---|
| 9,192,379 | B2 | 11/2015 | Aranyi et al. |
| 9,192,384 | B2 | 11/2015 | Bettuchi |
| 9,198,644 | B2 | 12/2015 | Balek et al. |
| 9,198,661 | B2 | 12/2015 | Swensgard |
| 9,204,876 | B2 | 12/2015 | Cappola et al. |
| 9,216,019 | B2 | 12/2015 | Schmid et al. |
| 9,216,020 | B2 | 12/2015 | Zhang et al. |
| 9,220,500 | B2 | 12/2015 | Swayze et al. |
| 9,220,501 | B2 | 12/2015 | Baxter, III et al. |
| 9,220,502 | B2 | 12/2015 | Zemlok et al. |
| 9,232,941 | B2 | 1/2016 | Mandakolathur Vasudevan et al. |
| 9,232,944 | B2 | 1/2016 | Cappola et al. |
| 9,237,891 | B2 | 1/2016 | Shelton, IV |
| 9,254,180 | B2 | 2/2016 | Huitema et al. |
| 9,265,585 | B2 | 2/2016 | Wingardner et al. |
| 9,271,728 | B2 | 3/2016 | Gupta et al. |
| 9,277,919 | B2 | 3/2016 | Timmer et al. |
| 9,282,962 | B2 | 3/2016 | Schmid et al. |
| 9,283,054 | B2 | 3/2016 | Morgan et al. |
| 9,289,209 | B2 | 3/2016 | Gurumurthy et al. |
| 9,289,210 | B2 | 3/2016 | Baxter, III et al. |
| 9,289,225 | B2 | 3/2016 | Shelton, IV et al. |
| 9,295,464 | B2 | 3/2016 | Shelton, IV et al. |
| 9,295,465 | B2 | 3/2016 | Farascioni |
| 9,301,752 | B2 | 4/2016 | Mandakolathur Vasudevan et al. |
| 9,301,753 | B2 | 4/2016 | Aldridge et al. |
| 9,301,757 | B2 | 4/2016 | Williams |
| 9,307,965 | B2 | 4/2016 | Ming et al. |
| 9,307,986 | B2 | 4/2016 | Hall et al. |
| 9,307,989 | B2 | 4/2016 | Shelton, IV et al. |
| 9,314,246 | B2 | 4/2016 | Shelton, IV et al. |
| 9,320,518 | B2 | 4/2016 | Henderson et al. |
| 9,320,521 | B2 | 4/2016 | Shelton, IV et al. |
| 9,326,767 | B2 | 5/2016 | Koch, Jr. et al. |
| 9,332,987 | B2 | 5/2016 | Leimbach et al. |
| 9,345,477 | B2 | 5/2016 | Anim et al. |
| 9,345,478 | B2 | 5/2016 | Knodel |
| 9,345,481 | B2 | 5/2016 | Hall et al. |
| 9,345,780 | B2 | 5/2016 | Manoharan et al. |
| 9,351,727 | B2 | 5/2016 | Leimbach et al. |
| 9,351,732 | B2 | 5/2016 | Hodgkinson |
| 9,358,003 | B2 | 6/2016 | Hall et al. |
| 9,364,217 | B2 | 6/2016 | Kostrzewski et al. |
| 9,364,218 | B2 | 6/2016 | Scirica |
| 9,364,219 | B2 | 6/2016 | Olson et al. |
| 9,364,220 | B2 | 6/2016 | Williams |
| 9,364,233 | B2 | 6/2016 | Alexander, III et al. |
| 9,370,358 | B2 | 6/2016 | Shelton, IV et al. |
| 9,370,362 | B2 | 6/2016 | Petty et al. |
| 9,386,983 | B2 | 7/2016 | Swensgard et al. |
| 9,386,984 | B2 | 7/2016 | Aronhalt et al. |
| 9,386,988 | B2 | 7/2016 | Baxter, III et al. |
| 9,393,018 | B2 | 7/2016 | Wang et al. |
| 9,398,911 | B2 | 7/2016 | Auld |
| 9,402,604 | B2 | 8/2016 | Williams et al. |
| 9,421,014 | B2 | 8/2016 | Ingmanson et al. |
| 9,433,419 | B2 | 9/2016 | Gonzalez et al. |
| 9,433,420 | B2 | 9/2016 | Hodgkinson |
| 9,445,810 | B2 | 9/2016 | Cappola |
| 9,445,813 | B2 | 9/2016 | Shelton, IV et al. |
| 9,451,959 | B2 | 9/2016 | Patankar et al. |
| 9,468,438 | B2 | 10/2016 | Baber et al. |
| 9,468,439 | B2 | 10/2016 | Cappola et al. |
| 9,480,476 | B2 | 11/2016 | Aldridge et al. |
| 9,480,492 | B2 | 11/2016 | Aranyi et al. |
| 9,492,171 | B2 | 11/2016 | Patenaude |
| 9,498,212 | B2 | 11/2016 | Racenet et al. |
| 9,510,827 | B2 | 12/2016 | Kostrzewski |
| 9,517,065 | B2 | 12/2016 | Simms et al. |
| 9,517,066 | B2 | 12/2016 | Racenet et al. |
| 9,539,007 | B2 | 1/2017 | Dhakad et al. |
| 9,549,735 | B2 | 1/2017 | Shelton, IV et al. |
| 9,770,245 | B2 | 9/2017 | Swayze et al. |
| 10,624,636 | B2 | 4/2020 | Beardsley et al. |
| 2004/0108357 | A1 | 6/2004 | Milliman et al. |
| 2004/0199180 | A1 | 10/2004 | Knodel et al. |
| 2004/0199181 | A1 | 10/2004 | Knodel et al. |
| 2004/0243151 | A1 | 12/2004 | Demmy et al. |
| 2004/0267310 | A1 | 12/2004 | Racenet et al. |
| 2005/0006429 | A1 | 1/2005 | Wales et al. |
| 2005/0216055 | A1 | 9/2005 | Scirica et al. |
| 2006/0049229 | A1 | 3/2006 | Milliman et al. |
| 2006/0180634 | A1 | 8/2006 | Shelton et al. |
| 2006/0289602 | A1 | 12/2006 | Wales et al. |
| 2007/0073341 | A1 | 3/2007 | Smith et al. |
| 2007/0084897 | A1 | 4/2007 | Shelton et al. |
| 2007/0102472 | A1 | 5/2007 | Shelton |
| 2007/0106317 | A1 | 5/2007 | Shelton et al. |
| 2007/0119901 | A1 | 5/2007 | Ehrenfels et al. |
| 2007/0145096 | A1 | 6/2007 | Viola et al. |
| 2007/0170225 | A1 | 7/2007 | Shelton et al. |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0179528 | A1 | 8/2007 | Soltz et al. |
| 2007/0194079 | A1 | 8/2007 | Hueil et al. |
| 2007/0194082 | A1 | 8/2007 | Morgan et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0078800 | A1 | 4/2008 | Hess et al. |
| 2008/0078802 | A1 | 4/2008 | Hess et al. |
| 2008/0110961 | A1 | 5/2008 | Voegele et al. |
| 2008/0169328 | A1 | 7/2008 | Shelton |
| 2008/0169332 | A1 | 7/2008 | Shelton et al. |
| 2008/0169333 | A1 | 7/2008 | Shelton et al. |
| 2008/0287987 | A1 | 11/2008 | Boyden et al. |
| 2008/0296346 | A1 | 12/2008 | Shelton, IV et al. |
| 2008/0308602 | A1 | 12/2008 | Timm et al. |
| 2008/0308603 | A1 | 12/2008 | Shelton et al. |
| 2009/0001121 | A1 | 1/2009 | Hess et al. |
| 2009/0001130 | A1 | 1/2009 | Hess et al. |
| 2009/0090763 | A1 | 4/2009 | Zemlok et al. |
| 2009/0090766 | A1 | 4/2009 | Knodel |
| 2009/0242610 | A1 | 10/2009 | Shelton, IV et al. |
| 2009/0255974 | A1 | 10/2009 | Viola |
| 2009/0308907 | A1 | 12/2009 | Nalagatla et al. |
| 2010/0012703 | A1 | 1/2010 | Calabrese et al. |
| 2010/0069942 | A1 | 3/2010 | Shelton, IV |
| 2010/0127041 | A1 | 5/2010 | Morgan et al. |
| 2010/0133317 | A1 | 6/2010 | Shelton, IV et al. |
| 2010/0147921 | A1 | 6/2010 | Olson |
| 2010/0147922 | A1 | 6/2010 | Olson |
| 2010/0155453 | A1 | 6/2010 | Bombard et al. |
| 2010/0193566 | A1 | 8/2010 | Scheib et al. |
| 2010/0224668 | A1 | 9/2010 | Fontayne et al. |
| 2010/0249802 | A1 | 9/2010 | May et al. |
| 2010/0252611 | A1 | 10/2010 | Ezzat et al. |
| 2011/0006101 | A1 | 1/2011 | Hall et al. |
| 2011/0024477 | A1 | 2/2011 | Hall |
| 2011/0024478 | A1 | 2/2011 | Shelton, IV |
| 2011/0036891 | A1 | 2/2011 | Zemlok et al. |
| 2011/0084112 | A1* | 4/2011 | Kostrzewski .... A61B 17/07207 |
| | | | 227/176.1 |
| 2011/0087276 | A1 | 4/2011 | Bedi et al. |
| 2011/0101069 | A1 | 5/2011 | Bombard et al. |
| 2011/0114702 | A1 | 5/2011 | Farascioni |
| 2011/0121049 | A1 | 5/2011 | Malinouskas et al. |
| 2011/0147433 | A1 | 6/2011 | Shelton, IV et al. |
| 2011/0155787 | A1 | 6/2011 | Baxter, III et al. |
| 2011/0163146 | A1 | 7/2011 | Ortiz et al. |
| 2011/0163149 | A1 | 7/2011 | Viola |
| 2011/0192881 | A1 | 8/2011 | Balbierz et al. |
| 2011/0192882 | A1 | 8/2011 | Hess et al. |
| 2011/0192883 | A1 | 8/2011 | Whitman et al. |
| 2011/0204119 | A1 | 8/2011 | McCuen |
| 2011/0278343 | A1 | 11/2011 | Knodel et al. |
| 2011/0290856 | A1 | 12/2011 | Shelton, IV et al. |
| 2012/0016362 | A1 | 1/2012 | Heinrich et al. |
| 2012/0053406 | A1 | 3/2012 | Conlon et al. |
| 2012/0061446 | A1 | 3/2012 | Knodel et al. |
| 2012/0074200 | A1 | 3/2012 | Schmid et al. |
| 2012/0080478 | A1 | 4/2012 | Morgan et al. |

(56)   References Cited

U.S. PATENT DOCUMENTS

| | | | |
|---|---|---|---|
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0196297 A1 | 7/2015 | Stopek et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |

(56) References Cited

U.S. PATENT DOCUMENTS

| | | |
|---|---|---|
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0100837 A1 | 4/2016 | Huang |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0367701 A1* | 12/2017 | Park ........... A61B 17/07207 |
| 2018/0317908 A1 | 11/2018 | Kostrzewski |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1621141 A2 | 2/2006 |
| EP | 1785098 | 5/2007 |
| EP | 1952769 A2 | 8/2008 |
| EP | 2090253 A2 | 8/2009 |
| EP | 2090254 A1 | 8/2009 |
| EP | 2311387 A1 | 4/2011 |
| EP | 2583630 A2 | 4/2013 |
| EP | 2586382 A2 | 5/2013 |
| EP | 2907456 A1 | 8/2015 |
| EP | 3175799 A1 | 6/2017 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2006043451 A | 2/2006 |
| JP | 2007130470 A | 5/2007 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |

(56)           References Cited

FOREIGN PATENT DOCUMENTS

| WO | 2009071070 | A2 | 6/2009 |
| WO | 2015191887 | A1 | 12/2015 |

OTHER PUBLICATIONS

Japanese Office Action dated Aug. 8, 2022, issued in corresponding JP Application No. 2018153103, 9 pages.
Australian Office Action dated Jul. 3, 2023, issued in corresponding Australian Appln. No. 2018206782, 4 pages.
Japanese Office Action dated Apr. 18, 2024, issued in corresponding JP Appln. No. 2022178013, 4 pages.
Notice of Allowance for Japanese Patent Application No. 2022-178013 mailed Apr. 21, 2025, 2 pages.

* cited by examiner

SURGICAL STAPLING DEVICE WITH FLOATING STAPLE CARTRIDGE

CROSS REFERENCE TO RELATED APPLICATION

This application is a continuation of U.S. patent application Ser. No. 17/712,748, filed Apr. 4, 2022, which is a continuation of U.S. patent application Ser. No. 16/829,379, filed Mar. 25, 2020, which is a continuation of U.S. patent application Ser. No. 15/684,223, filed Aug. 23, 2017, now U.S. Pat. No. 10,624,636, the disclosure of each of which is incorporated by reference herein in its entirety.

BACKGROUND

1. Technical Description

The present disclosure is directed to a surgical stapling device and, more particularly, to a surgical stapling device including a tool assembly having a staple cartridge that is supported on a compressible base to accommodate tissues of different thicknesses.

2. Background of Related Art

Surgical stapling devices for ejecting staples to join tissue or tissue segments in a fast and efficient manner in a variety of surgical procedures, e.g., anastomoses procedures, are well known. Surgical stapling devices include a tool assembly having a cartridge assembly and an anvil assembly. The cartridge assembly and the anvil assembly define tissue contact surfaces that define a tissue gap when the tool assembly is in a clamped position. The tissue gap is dimensioned to receive tissue of a given thickness range to effect hemostasis. If the tissue positioned between the jaws is outside the defined range, either too thick or too thin, the tissue contact surfaces of the cartridge and anvil assemblies may not be properly positioned during firing of the stapling device to provide effective hemostasis. In addition, if the tissue thickness is misidentified by the clinician or if the tissue thickness falls near the outer edges of the range for a given staple size, the likelihood of ineffective hemostasis is increased.

Accordingly, a continuing need exists in the suturing arts for a surgical stapling device that is capable of providing effective hemostasis for a greater range of tissue thicknesses.

SUMMARY

In one aspect of the disclosure, a cartridge assembly includes a cartridge channel having a bottom wall and side walls that define a recess. Each of the side walls has a first end secured to the bottom wall and a second end spaced from the bottom wall defining an elongated slot. A staple cartridge defines a longitudinal axis and includes an upper wall defining a tissue contact surface and side walls. The upper wall extends radially outward of the side walls of the staple cartridge to define a longitudinally extending shoulder that is positioned adjacent to each of the side walls of the staple cartridge. The staple cartridge is dimensioned to be received within the recess of the cartridge channel such that the shoulders of the staple cartridge rest atop the side walls of the cartridge channel. A compression strip is supported in each of the elongated slots defined in the second end of the side walls of the cartridge channel. The elongated slots and the compression strips are configured to interlock to secure the compression strips to the cartridge channel.

In another aspect of the disclosure, a cartridge assembly includes a cartridge channel having a bottom wall and side walls defining a recess, and a staple cartridge defining a longitudinal axis and supporting a plurality of staples and a plurality of pushers. The staple cartridge is received within the recess of the cartridge channel. The staple cartridge has an upper wall defining a tissue contact surface and a plurality of staple retention slots. A compression pad is positioned between the bottom wall of the cartridge channel and the staple cartridge.

In embodiments, each of the compression strips includes a connecting portion that is received within the longitudinal slot.

In some embodiments, the connecting portion of each of the compression strips and the elongated slot are dove-tail shaped.

In certain embodiments, the second end of each of the side walls of the cartridge channel includes cutouts, the cutouts intersecting the elongated slot to divide the elongated slot into a plurality of segments.

In embodiments, each of the compression strips is formed of a plurality of segments, and each of the plurality of segments of the compression strips has a length that corresponds to a length of one of the plurality of segments of the elongated slots.

In some embodiments, each of the compression strips is formed from an elastic material.

In certain embodiments, the cartridge assembly includes a support plate and the staple cartridge includes staples and pushers and defines an open end opposite to the upper wall. The support plate is supported on the open end of the staple cartridge to retain the staples and pushers within the staple cartridge.

In embodiments, the staple cartridge and the support plate define a gap with the bottom wall of the cartridge channel.

In some embodiments, a compression pad is positioned in the gap between the staple cartridge and the bottom wall of the cartridge channel.

In certain embodiments, the cartridge channel and the staple cartridge each define a knife slot, and the compression pad includes a first half positioned on one side of the knife slots and a second half positioned on the other side of the knife slots.

In some embodiments, the compression pad is secured to the bottom wall of the cartridge channel using an adhesive.

In embodiments, the compression pad is formed from an elastic material.

BRIEF DESCRIPTION OF THE DRAWINGS

Various embodiments of the presently disclosed tool assembly are described herein below with reference to the drawings, wherein.

DETAILED DESCRIPTION OF EMBODIMENTS

Figure 1:
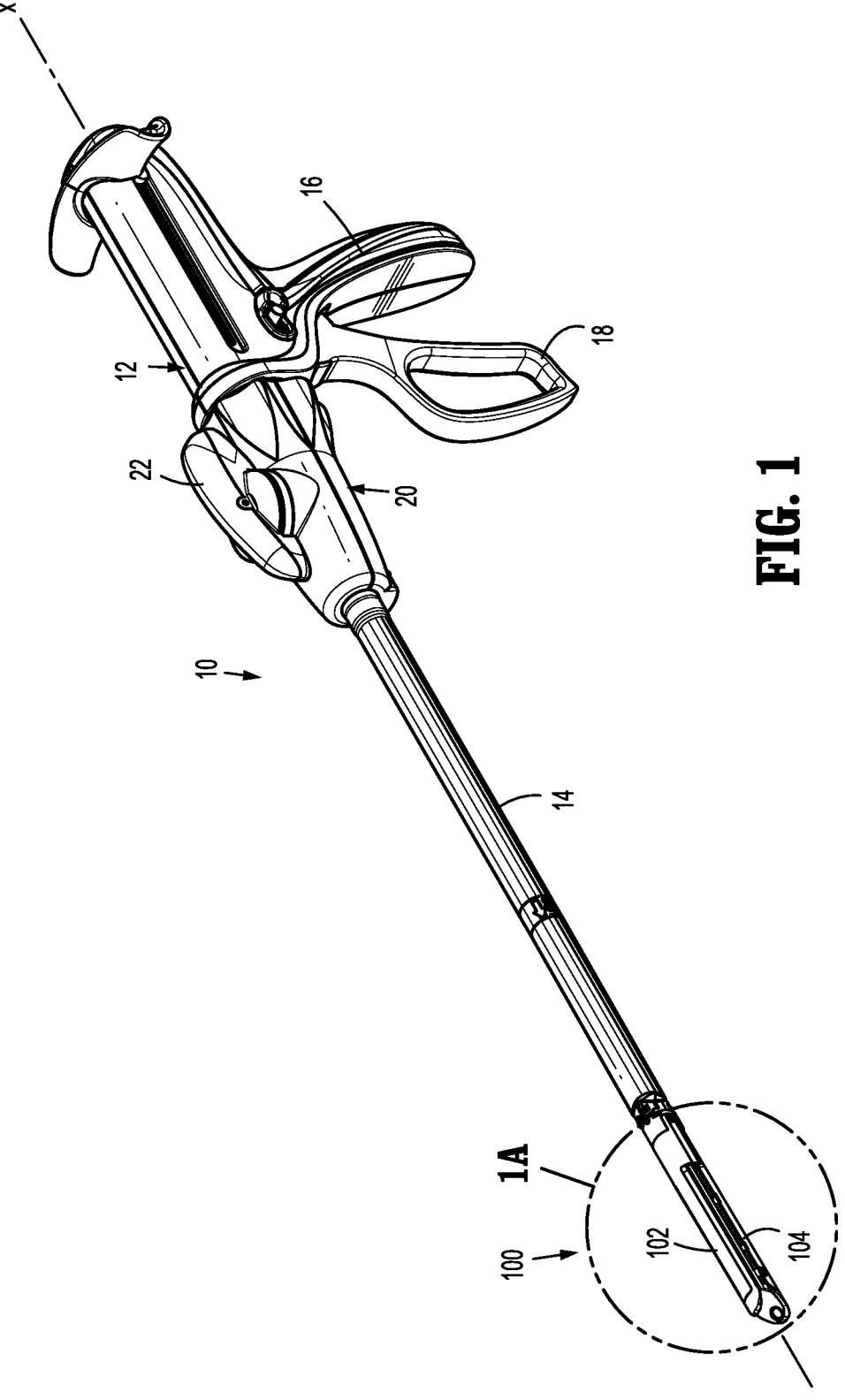
FIG. 1 is a side perspective view of a surgical stapling device including an exemplary embodiment of the presently disclosed tool assembly in a clamped position.

The presently disclosed surgical stapling device including a tool assembly with a floating staple cartridge will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. In addition, the term clinician is used generally to refer to medical personnel including doctors, nurses, and support personnel.

The presently disclosed surgical stapling device includes a tool assembly having an anvil assembly and a cartridge assembly including a cartridge channel and a staple cartridge supported within the cartridge channel. The cartridge assembly includes a cartridge channel having a pair of spaced sidewalls and a bottom wall. The cartridge assembly includes compression strips that are supported on upper edges of the side walls of the cartridge channel and are positioned to support the staple cartridge. In embodiments, each of the compression strips includes a connecting portion and the upper edge of each of the side walls defines a slot that is configured to receive the connecting portion of a respective compression strip to secure the compression strips to the side walls of the cartridge channel. The compression strips allow the staple cartridge to move or float in relation to the anvil assembly of the tool assembly to accommodate tissues of different thicknesses.

In some embodiments, the tool assembly also includes a compressible pad that is supported on the bottom wall of the channel. The staple cartridge is supported on the compressible pad within the cartridge channel such that the staple cartridge can move or float within the cartridge channel.

FIG. 1 illustrates an exemplary embodiment of the presently disclosed surgical stapling device shown generally as 10. The stapling device 10 includes a handle assembly 12, a body portion 14 that defines a longitudinal axis "X" and extends from a distal portion of the handle assembly 12, and a tool assembly 100 supported on a distal portion of the body portion 14. In embodiments, the handle assembly 12 includes a stationary hand grip 16, a firing trigger 18, a rotation knob 20, and an articulation lever 22. The firing trigger 18 is actuatable to move the tool assembly 100 between an unclamped position (FIG. 2) and a clamped position (FIG. 1A) and to fire the stapling device 10. The articulation lever 22 is rotatable to pivot the tool assembly 100 in relation to the body portion 14 about an axis transverse to the longitudinal axis "X". The rotation knob 20 pivotally supports the body portion 14 and the tool assembly 100 on the distal portion of the handle assembly 12. Rotation of the rotation knob 20 in relation to the handle assembly 12 causes corresponding rotation of the body portion 14 and tool assembly 100 in relation to the handle assembly 12.

For a detailed description of a handle assembly 12 including the firing trigger 18, rotation knob 20, and articulation lever 22, and other components of the stapling device 10 including the body portion 14, see U.S. Pat. No. 8,418,904 ("the '904 patent") which is incorporated herein by reference in its entirety. Although the presently disclosed tool assembly 100 is illustrated as part of a manually powered surgical stapling device 10, it is also envisioned that the tool assembly 100 could be incorporated into a powered surgical stapling device such as disclosed in U.S. Pat. Nos. 9,055,943 and 8,806,973 and U.S. Publication No. 2015/0076206 which are also incorporated herein by reference in their entirety.

Figure 1A:
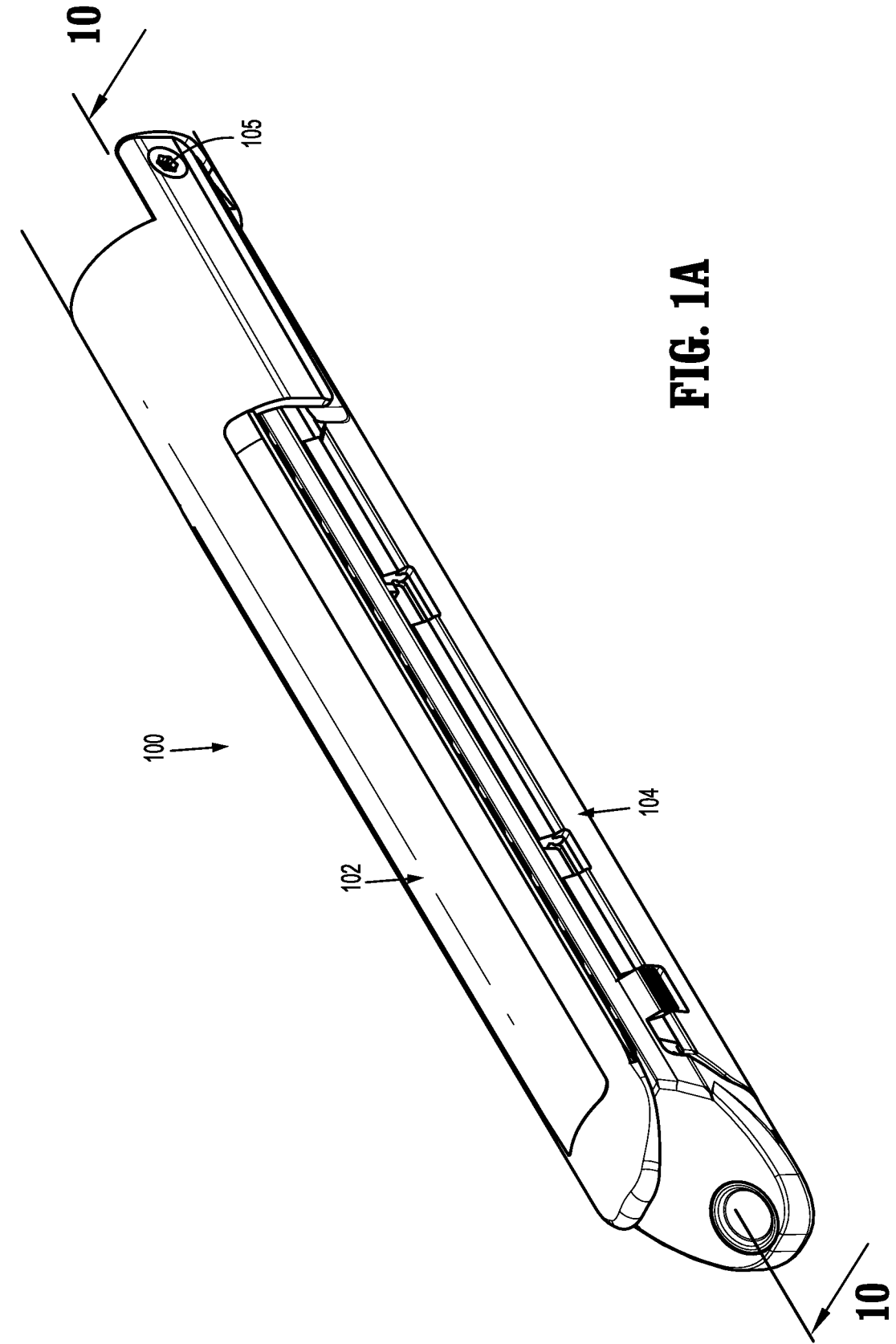
FIG. 1A is an enlarged view of the indicated area of detail shown in FIG. 1.
Figure 2:
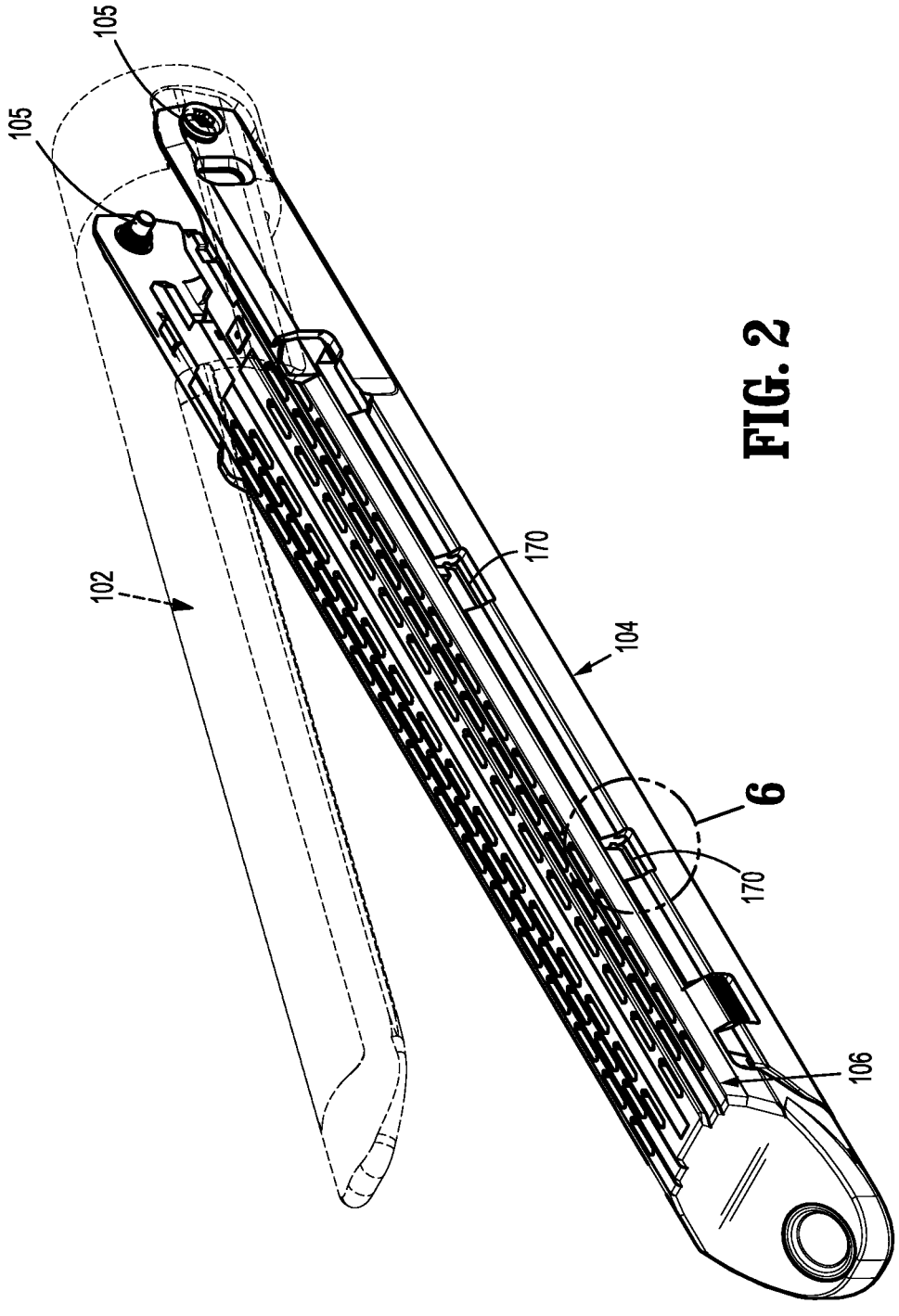
FIG. 2 is a side perspective view of the tool assembly of FIG. 1 in an unclamped position with an anvil assembly of the tool assembly shown in phantom.

Referring to FIGS. 1A and 2, the tool assembly 100 includes an anvil assembly 102 and a cartridge assembly 104. A proximal portion of the anvil assembly 102 is pivotally coupled to a proximal portion of the cartridge assembly 104 by a pair of pivot members 105 such that the anvil assembly 102 is pivotal in relation to the cartridge assembly 104 to move the tool assembly 100 between an unclamped position (FIG. 2) and a clamped position (FIG. 1A). It is envisioned that the cartridge assembly could also be pivotally supported to the anvil assembly 102. Although not shown, the anvil assembly 102 includes a tissue contact surface that includes a plurality of staple deforming depressions. See, e.g., the anvil assembly disclosed in the '904 patent.

Figures 3, 3A:
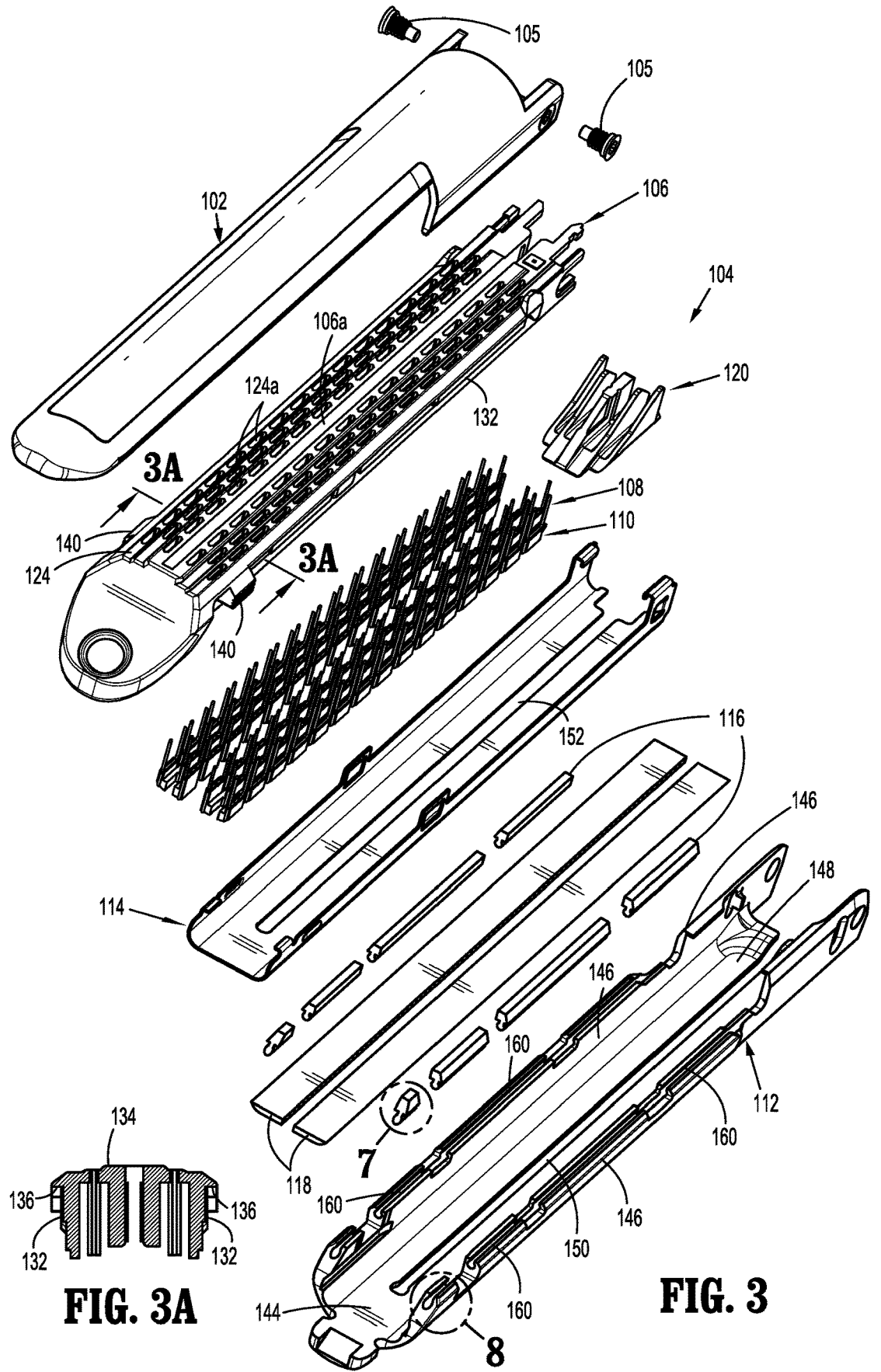
FIG. 3 is a side, perspective, exploded view of a cartridge assembly of the tool assembly shown in FIG. 2.
FIG. 3A is a cross-sectional view taken along section line 3A-3A.

Referring to FIG. 3, in some embodiments the cartridge assembly 104 includes a staple cartridge 106 that supports a plurality of staples 108 and a plurality of pushers 110, a cartridge channel 112, a staple cartridge support plate 114, compression strips 116, compression pads 118, and an actuation sled 120. It is envisioned that the cartridge assembly 104 may include only compression strips 116 or compression pads 118 as discussed in further detail below. The staple cartridge 106 includes a tissue contact surface 124 (FIG. 3) that defines a central knife slot 106a, and a plurality of rows of laterally spaced staple retention slots 124a in the tissue contact surface 124. In embodiments, the tissue contact surface 124 is stepped downwardly from the central knife slot 106a towards the outer edge of the staple cartridge 106. Alternately, the tissue contact surface 124 of the staple cartridge 106 can be planar. Each staple retention slot 124a receives one of the staples 108 and a respective pusher 110.

Figures 10, 11:
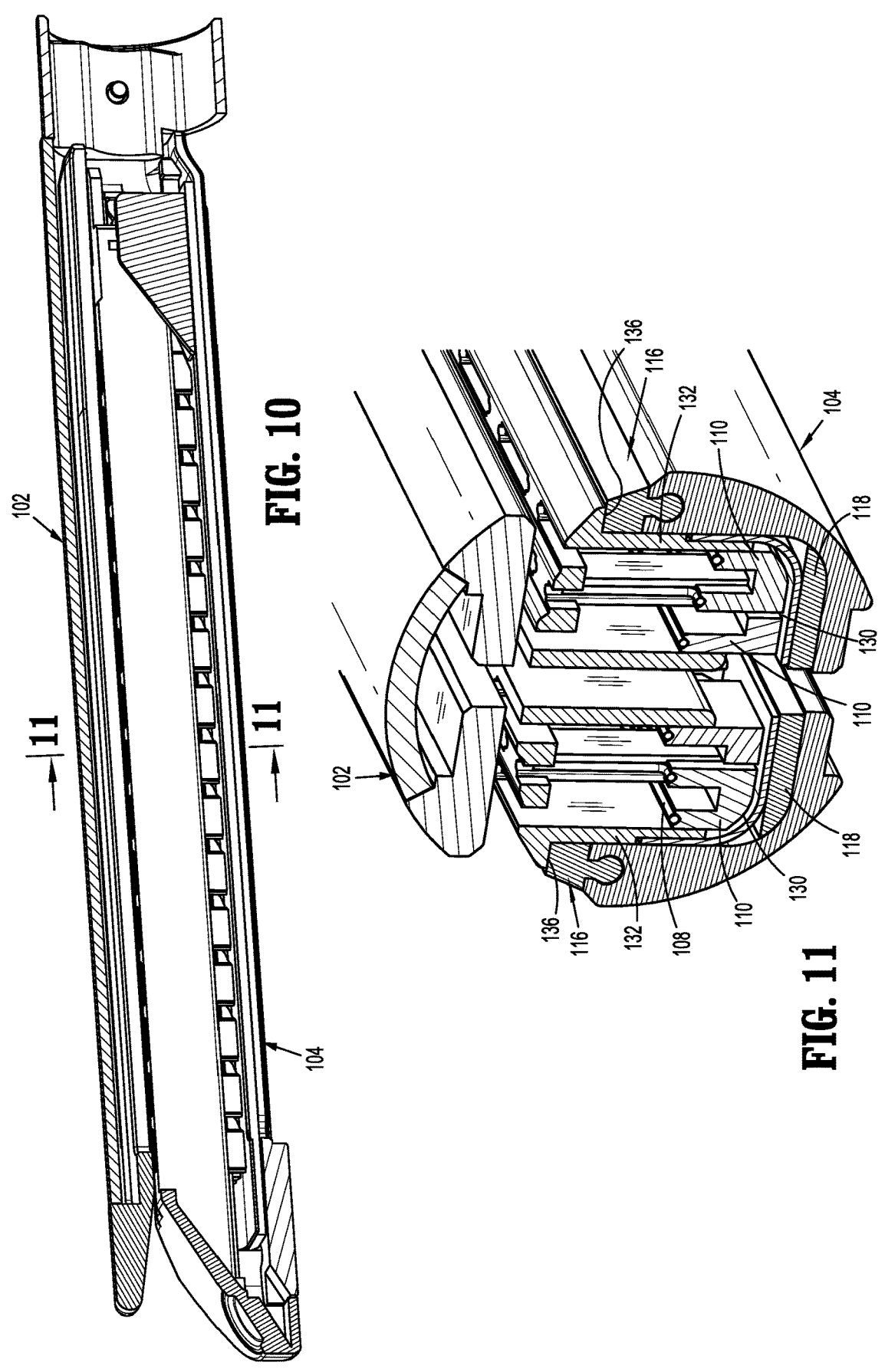
FIG. 10 is a cross-sectional view taken along section line 10-10 of FIG. 1A.
FIG. 11 is a cross-sectional view taken along section line 11-11 of FIG. 10.
Figure 12:
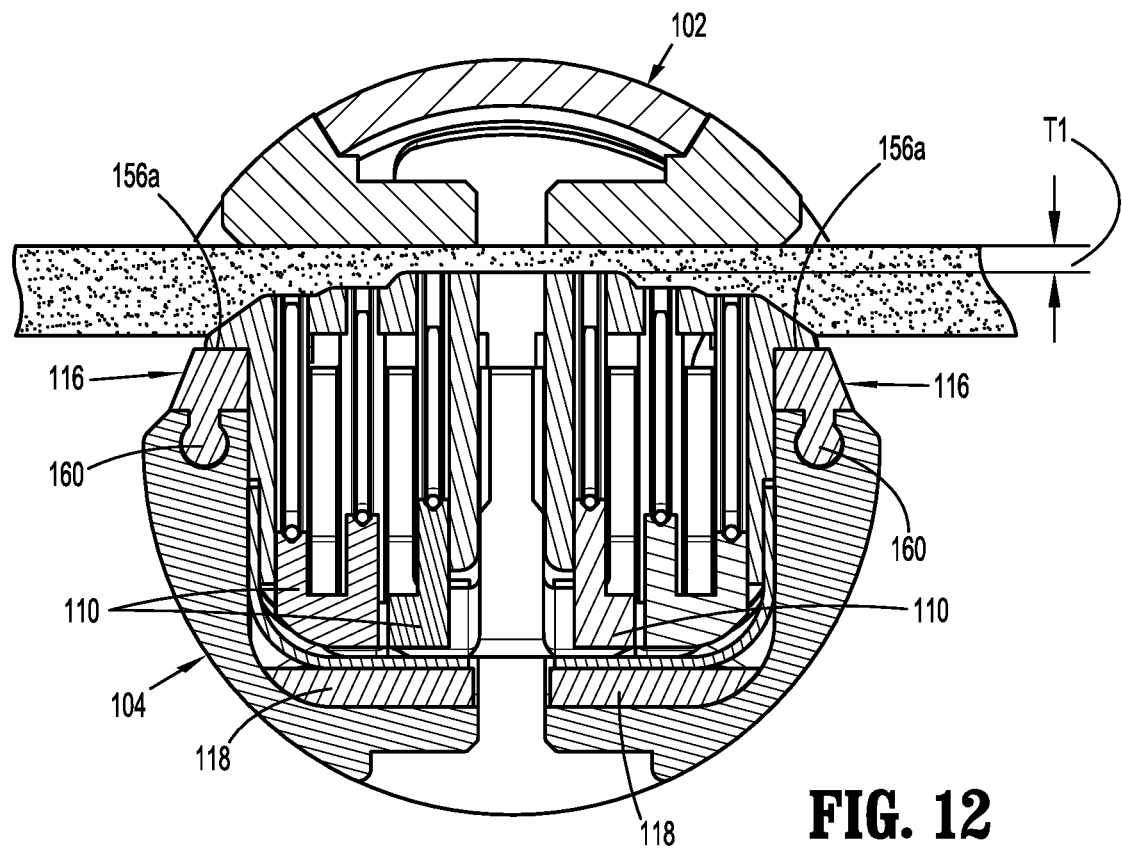
FIG. 12 is a cross-sectional view taken along section line 11-11 of FIG. 10 with the tool assembly clamped on relatively thin tissue.
Figure 13:
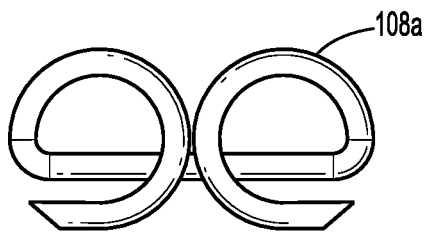
FIG. 13 is a side view of a staple of the cartridge assembly of FIG. 12 after the staple is deformed in thin tissue.

The support plate 114 of the cartridge assembly 104 is secured to an open, lower end of the staple cartridge 106 opposite to the tissue contact surface 124 by a snap-fit or other type connection. The support plate 114 covers the open lower end of the staple cartridge 106 to retain the staples 108 and pushers 110 within the staple cartridge 106. The staple cartridge 106 also defines a plurality of longitudinal slots 130 (FIG. 11). The longitudinal slots 130 communicate with the open, lower end of the staple cartridge 106 and the staple retention slots 124a to accommodate the staple pushers 110 and facilitate passage of the actuation sled 120 through the staple cartridge 106. As known in the art, advancement of the actuation sled 120 through the staple cartridge 106 lifts the pushers 110 within the retention slots 124a to eject the staples 108 from the retention slots 124a. See, e.g., the '904 patent for a detailed description of the operation, and interaction of the actuation sled 120 and pushers 110.

The staple cartridge 106 includes opposite sidewalls 132 and an upper wall 134 that defines the tissue contact surface 124 and the staple retention slots 124a. The upper wall 134 extends radially outward of the side walls 132 to define shoulders 136 (FIG. 3A). The staple cartridge 106 also includes protrusions 140 (FIG. 3) that extend radially outwardly of each of the side walls 132 of the staple cartridge 106 and facilitate securement of the staple cartridge 106 within the cartridge channel 112.

Figures 4, 5:
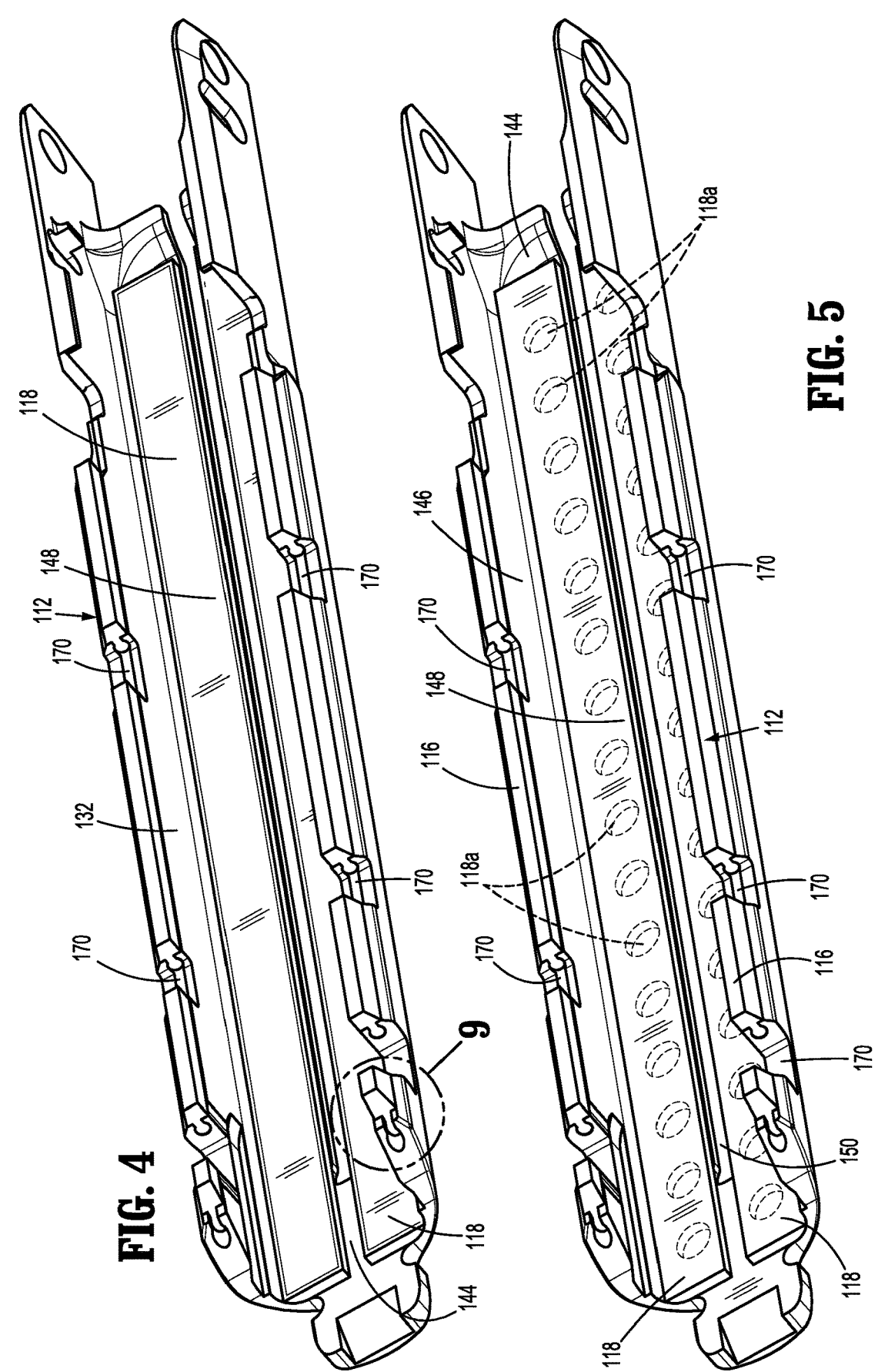
FIG. 4 is a side perspective view of a channel member of the cartridge assembly shown in FIG. 3 with compression strips attached to side walls of the channel member.
FIG. 5 is a side perspective view of the channel member of the cartridge assembly shown in FIG. 4 with the compression strips and a compression pad supported on the channel member.
Figures 6, 7, 8, 9:
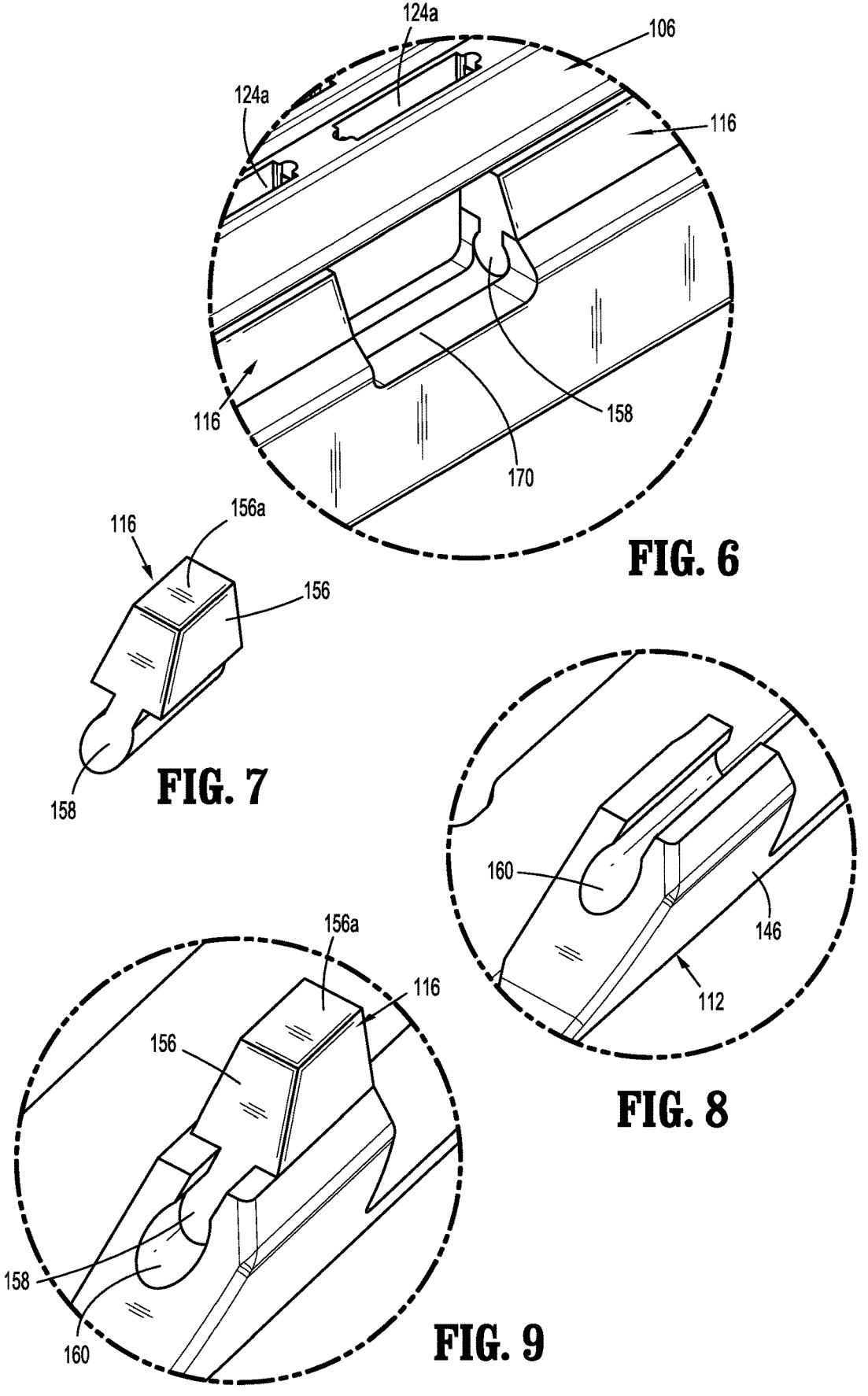
FIG. 6 is an enlarged view of the indicated area of detail shown in FIG. 2.
FIG. 7 is an enlarged view of the indicated area of detail shown in FIG. 3.
FIG. 8 is an enlarged view of the indicated area of detail shown in FIG. 3.
FIG. 9 is a perspective view of the indicated area of detail shown in FIG. 8 as the compression strip is attached to the side wall of the channel member.

Referring also to FIGS. 4 and 5, the cartridge channel 112 includes a bottom wall 144 and spaced side walls 146 that together define a recess 148 that is dimensioned to receive the staple cartridge 106 and support plate 114 when the staple cartridge 106 and the support plate 114 are assembled. The bottom wall 144 defines a central longitudinal knife slot 150 that is aligned with the central knife slot 106a defined in the staple cartridge 106 as well as a longitudinal knife slot 152 defined by the support plate 114. The knife slots 106a, 150 and 152 are dimensioned to facilitate passage of a drive member and knife (not shown) through the staple cartridge 106. See, e.g., the '904 patent for a detailed description of an exemplary embodiment of a drive member and knife of a surgical stapling device.

Referring also to FIGS. 3 and 6-9, the compression strips 116 are formed of a compressible and/or elastic material. Each of the compression strips 116 includes a support portion 156 and a connecting portion 158. In embodiments, the support portion 156 of each of the compression strips 116 defines a flat surface 156a that is positioned and configured to support the shoulders 136 of the staple cartridge 106 (FIG. 3A).

In embodiments, the spaced side walls 146 of the cartridge channel 112 each define a retention slot 160 (FIG. 8) that is configured to receive a connecting portion 158 of the compression strips 116. In embodiments, the retention slots 160 and the connecting portions 158 of the compression strips 116 have interlocking configurations which mate to securely fasten the compression strips 116 within the retention slots 160. In some embodiments, the retention slots 160 and the connecting portion of the compression strips 116 each include have a dove-tail configuration although other interlocking configurations are envisioned, e.g., T-shaped slots, etc. The connecting portion 158 of the compression strips 116 are slidably received within the retention slots 160 to secure the compression strips 116 to the upper edges of the side walls 146 of the cartridge channel 112. In addition, adhesives, welding, friction fitting, or the like can be used to secure the compression strips from moving axially within the slots 160

Referring briefly back to FIGS. 4 and 5, the side walls 146 of the cartridge channel 112 each include a plurality of notches 170. The notches 170 provide access to ends of the retention slots 160 at a plurality of locations along the side walls 146 of the cartridge channel 112 to allow the connecting portions 158 of the compression strips 116 to be inserted into the retention slots 160 at multiple locations along the side walls 146.

Referring again to FIGS. 3 to 5, 10 and 11, in embodiments, the compression pads 118 are supported on the bottom wall 144 of the cartridge channel 112 between the bottom wall 144 and the support plate 114 of the cartridge assembly 104 (FIG. 11) on opposite sides of the knife slot 150. As discussed above regarding the compression strips 116, the compression pads 118 are formed of an elastic and/or compressible material and support the staple cartridge 106 to facilitate movement of the staple cartridge 106 in relation to the anvil assembly 102 during clamping and firing of the surgical stapling device 10. In embodiments, the compression pads 118 include cut outs 118a that provide space for expansion of the compression pad 118 during firing. Although shown as being circular, the cut outs 118a can be of any configuration.

Referring to FIGS. 10-13, when thin tissue T1 is clamped between the tissue contact surface 124 of the staple cartridge 106 and the tissue contact surface 102a of the anvil assembly 102 and the surgical stapling device 10 is fired, the forces applied to the compression strips 116 and the compression pads 118 is minimal such that the compressible strips 116 and pads 118 undergo minimal deformation or compression. As such, very little movement of the staple cartridge 106 in relation to the anvil assembly 102 occurs. Thus, the staple cartridge 106 remains in close relation to the anvil assembly 102 and the staple 108a (FIG. 13) undergoes substantial deformation.

Figure 14:
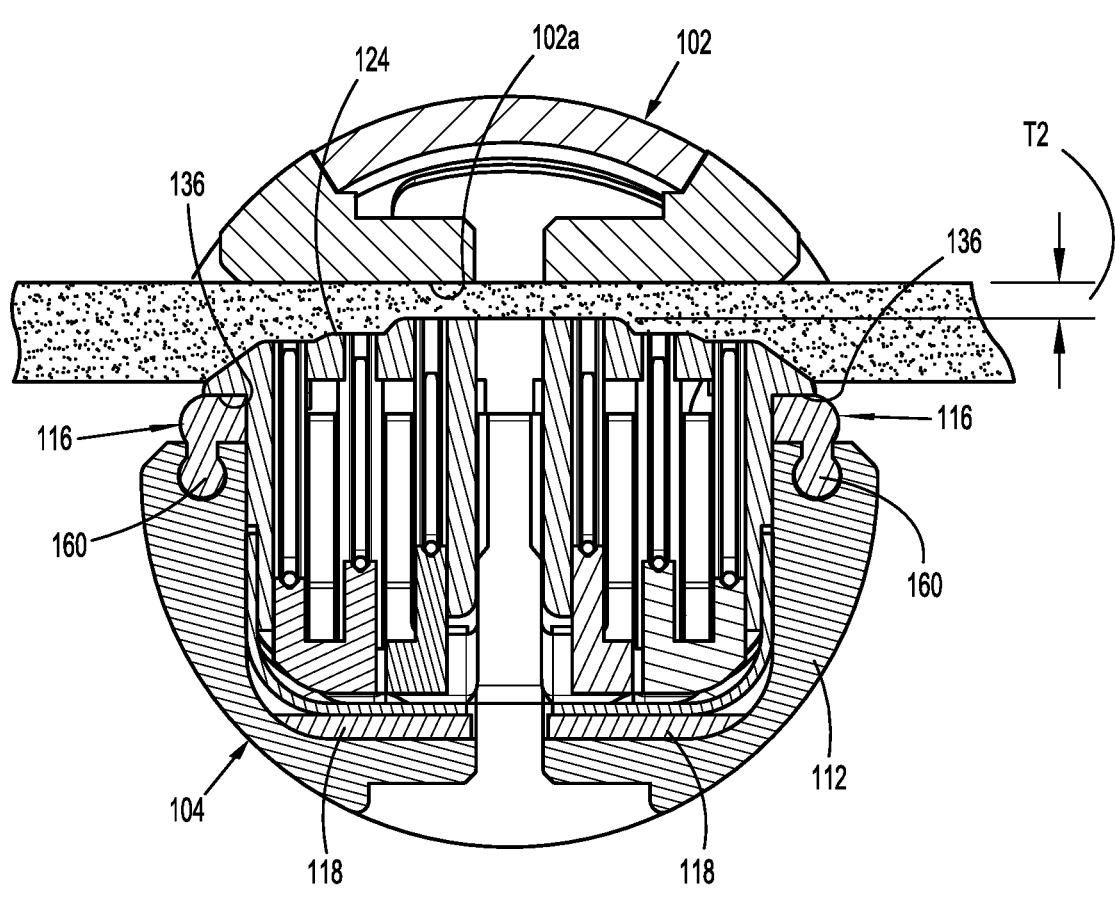
FIG. 14 is a cross-sectional view taken along section line 11-11 of FIG. 10 with the tool assembly clamped on tissue having a relatively moderate thickness.
Figure 15:
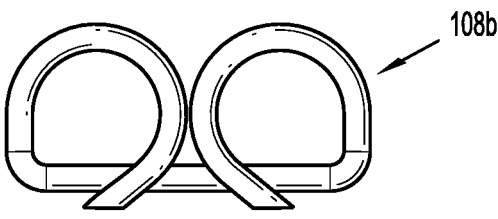
FIG. 15 is a side view of a staple of the cartridge assembly of FIG. 14 after the staple is deformed in the tissue having a relatively moderate thickness.

Referring to FIGS. 14 and 15, when thicker tissue T2 is clamped between the tissue contact surface 124 of the staple cartridge 106 and the tissue contact surface 102a of the anvil assembly 102 and the surgical stapling device 10 is fired, the forces applied to the compression strips 116 and the compression pads 118 increases such that the compressible strips 116 and compression pads 118 undergo more substantial deformation or compression. As such, the staple cartridge 106 moves further downwardly away from the anvil assembly 102 to compensate for the thicker tissue T2. Thus, the staple cartridge 106 becomes spaced further from the anvil assembly 102 and the staple 108b undergoes more substantial deformation.

Figure 16:
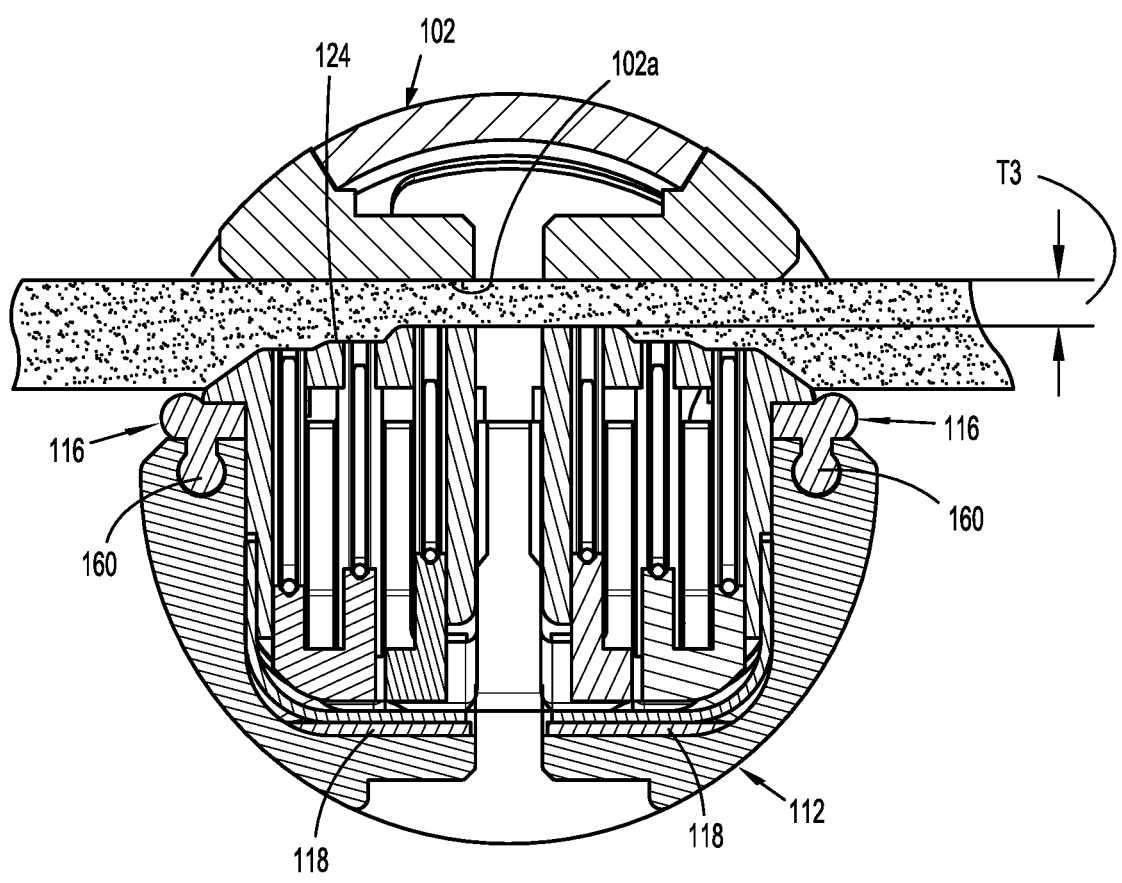
FIG. 16 is a cross-sectional view taken along section line 11-11 of FIG. 10 with the tool assembly clamped on relatively thick tissue.
Figure 17:
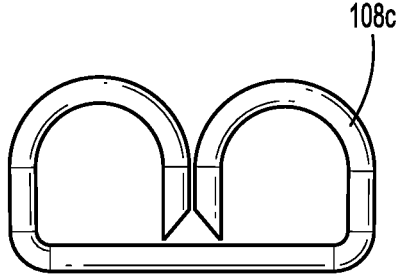
FIG. 17 is a side view of a staple of the cartridge assembly of FIG. 16 after the staple is deformed in the relatively thick tissue.

Referring to FIGS. 16 and 17, when even thicker tissue T3 is clamped between the tissue contact surface 124 of the staple cartridge 106 and the tissue contact surface 102a of the anvil assembly 102 and the surgical stapling device 10 is fired, the forces applied to the compression strips 116 and the compression pads 118 increases even further such that the compressible strips 116 and pads 118 undergo even more substantial deformation or compression. As such, the staple cartridge 106 moves further downwardly away from the anvil assembly 102 to compensate for the thicker tissue T3. Thus, the staple cartridge 106 becomes spaced even further from the anvil assembly 102 and the staple 108b undergoes even more substantial deformation.

Although the surgical stapling device 10 is illustrated to include both compression strips 116 and compression pads 118, it is envisioned that the surgical stapling device need only include the strips 116 or the pads 118.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A tool assembly comprising:

an anvil assembly having a first tissue contacting surface;

a cartridge assembly coupled to the anvil assembly to facilitate movement of the tool assembly between open and clamped positions, the cartridge assembly including a cartridge channel and a staple cartridge, the staple cartridge having a length and including a cartridge body of unitary construction, staples, pushers, and an actuation sled, the cartridge body having a second tissue contacting surface and defining a cartridge knife slot and a plurality of staple slots positioned on opposite sides of the knife slot, the staples received in the staple slots, the cartridge channel having a bottom wall and spaced side walls that define a recess, the bottom wall defining a channel knife slot that is longitudinally aligned with the cartridge knife slot, the staple cartridge received within the recess, the first tissue contacting surface being in juxtaposed spaced relation to the second tissue contacting surface when the tool assembly is in the clamped position;

at least one compression pad positioned on the bottom wall of the cartridge channel, the at least one compression pad being formed of a compressible material and supporting the staple cartridge along a majority of the length of the staple cartridge within the recess of the cartridge channel to facilitate movement of the staple cartridge within the recess of cartridge channel, one of the at least one compression pad positioned on each side of the channel knife slot; and a plurality of compression strips that each extend substantially in a first direction, wherein each of the plurality of compression strips are spaced from one another by a corresponding notch of a plurality of notches, the plurality of compression strips being formed of a compressible material, wherein a protrusion of at least one of the plurality of compression strips is configured to fit into a retention cavity defined within a spaced side wall of the cartridge channel, wherein the protrusion extends from the at least one of the plurality of compression strips substantially in a second direction that is perpendicular to the first direction, and wherein the protrusion, when fit into the retention cavity, is disposed between an outside surface of the spaced side wall and an inside surface of the spaced side wall opposite the outside surface.

2. The tool assembly of claim 1, wherein the staple cartridge includes a staple cartridge support plate secured to a lower end of the cartridge body, the at least one compression pad positioned between the staple cartridge support plate and the bottom wall of the cartridge channel.

3. The tool assembly of claim 1, wherein the actuation sled is movable through the cartridge body of the staple cartridge into sequential engagement with the pushers to eject the staples from the staple slots.

4. The tool assembly of claim 1, wherein the at least one compression pads define spaced cut outs to facilitate expansion of the at least one compression pad into the cut outs.

5. The tool assembly of claim 4, wherein the cut outs are circular.

6. The tool assembly of claim 5, wherein the cutouts are longitudinally aligned with each other along a length of the at least one compression pad.

7. A surgical stapling device comprising:

a handle assembly;

an elongate body portion having a proximal portion and a distal portion, the proximal portion secured to the handle assembly; and a tool assembly supported on the distal portion of the elongate body portion, the tool assembly including:

an anvil assembly having a first tissue contacting surface;

a cartridge assembly coupled to the anvil assembly to facilitate movement of the tool assembly between open and clamped positions, the cartridge assembly including a cartridge channel and a staple cartridge, the staple cartridge having a length and including a cartridge body of unitary construction, staples, pushers, and an actuation sled, the cartridge body having a second tissue contacting surface and defining a cartridge knife slot and a plurality of staple slots positioned on opposite sides of the knife slot, the staples received in the staple slots, the cartridge channel having a bottom wall and spaced side walls that define a recess, the bottom wall defining a channel knife slot that is longitudinally aligned with the cartridge knife slot, the staple cartridge received within the recess, the first tissue contacting surface being in juxtaposed relation to the second tissue contacting surface when the tool assembly is in the clamped position;

at least one compression pad positioned on the bottom wall of the cartridge channel, the at least one compression pad being formed of a compressible material and supporting the staple cartridge along a majority of the length of the staple cartridge within the recess of the cartridge channel to facilitate movement of the staple cartridge within the recess of cartridge channel, one of the at least one compression pad positioned on each side of the channel knife slot; and at least two compression strips that extend substantially in a first direction, the at least two compression strips being formed of a compressible material, wherein each compression strip includes a protrusion of configured to fit into a retention cavity defined within a spaced side wall of the cartridge channel, wherein each of the compression strips is spaced apart in the first direction by a notch in the side wall, wherein each of the protrusions extends from the respective compression strip substantially in a second direction that is perpendicular to the first direction, and wherein each of the protrusions, when fit into the retention cavity, is disposed between an outside surface of the spaced side wall and an inside surface of the spaced side wall opposite the outside surface.

8. The surgical stapling device of claim 7, wherein the staple cartridge includes a staple cartridge support plate secured to a lower end of the cartridge body, the at least one compression pad positioned between the staple cartridge support plate and the bottom wall of the cartridge channel.

9. The surgical stapling device of claim 7, wherein the actuation sled is movable through the cartridge body of the staple cartridge into sequential engagement with the pushers to eject the staples from the staple slots.

10. The surgical stapling device of claim 7, wherein the at least one compression pad define spaced cut outs to facilitate expansion of the at least one compression pad into the cut outs.

11. The surgical stapling device of claim 10, wherein the cut outs are circular.

12. The surgical stapling device of claim 11, wherein the cutouts are longitudinally aligned with each other along a length of the at least one compression pad.

13. A cartridge assembly comprising:
a cartridge channel comprising:
a bottom wall; and
a first side wall, on one side of the bottom wall, including a plurality of notches; and
a second side wall, on another side of the bottom wall, including a plurality of notches;
a staple cartridge including a cartridge body;
a first compression strip extending along the first side wall between a first notch and a second notch of the first side wall; and a second compression strip, spaced apart from the first compression strip by the second notch, extending along the first side wall between the second notch and a third notch of the first side wall.

14. The cartridge assembly of claim 13, further comprising a compression pad, wherein the staple cartridge includes a staple cartridge support plate secured to a lower end of the cartridge body, wherein the compression pad is positioned between the staple cartridge support plate and the bottom wall of the cartridge channel.

15. The cartridge assembly of claim 13, further comprising:
a third compression strip along the second wall between a first notch and a second notch of the second side wall; and
a fourth compression strip along the second wall between the second notch and a third notch of the second side wall.

16. The cartridge assembly of claim 13, wherein the first side wall includes an elongated slot between the first notch and the second notch.

17. The cartridge assembly of claim 13, wherein the first compression strip includes a connecting portion that protrudes into the elongated slot to mate the first compression strip with the first side wall.

18. The cartridge assembly of claim 13, wherein the first compression strip is formed from an elastic material.

* * * * *